United States Patent [19]

Failli et al.

[11] Patent Number: 5,480,988

[45] Date of Patent: Jan. 2, 1996

[54] CARBAMATES OF RAPAMYCIN

[75] Inventors: Amedeo A. Failli, Princeton Junction, N.J.; Oleg I. Bleyman, Holland, Pa.; Wenling Kao, Paoli, Pa.; Magid A. Abou-Gharbia, Glen Mills, Pa.

[73] Assignee: American Home Products Corporation, Madison, N.J.

[21] Appl. No.: 284,764

[22] Filed: Aug. 2, 1994

Related U.S. Application Data

[60] Continuation-in-part of Ser. No. 160,984, Dec. 1, 1993, abandoned, which is a division of Ser. No. 54,655, Apr. 23, 1993, Pat. No. 5,302,584, which is a continuation-in-part of Ser. No. 960,597, Oct. 13, 1992, abandoned.

[51] Int. Cl.$^6$ .................. C07D 498/16; A61K 31/395
[52] U.S. Cl. .................................................. 540/456
[58] Field of Search .................................................. 540/456

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,375,464 | 3/1983 | Sehgal et al. | 424/122 |
| 4,401,653 | 8/1983 | Eng | 424/114 |
| 4,650,803 | 3/1987 | Stella et al. | 514/291 |
| 4,885,171 | 12/1989 | Serendra et al. | 424/114 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 540/456 |
| 5,100,899 | 3/1992 | Calne | 514/291 |
| 5,102,876 | 4/1992 | Caufield | 540/456 |
| 5,118,677 | 6/1992 | Caufield | 540/456 |
| 5,118,678 | 6/1992 | Kao et al. | 540/446 |
| 5,120,842 | 6/1992 | Failli et al. | 540/456 |
| 5,130,307 | 7/1992 | Failli et al. | 540/456 |
| 5,138,051 | 8/1992 | Hughes et al. | 540/456 |
| 5,151,413 | 9/1992 | Caufield et al. | 540/456 |
| 5,169,851 | 12/1992 | Hughes et al. | 540/456 |
| 5,177,203 | 1/1993 | Failli et al. | 540/456 |
| 5,194,447 | 3/1993 | Kao | 540/456 |
| 5,221,670 | 6/1993 | Caufield | 514/183 |
| 5,233,036 | 8/1993 | Hughes | 540/183 |
| 5,260,300 | 11/1993 | Hu | 514/291 |
| 5,262,423 | 11/1993 | Kao | 540/456 |
| 5,286,730 | 2/1994 | Caufield et al. | 514/291 |
| 5,286,731 | 2/1994 | Caufield et al. | 514/291 |
| 5,302,584 | 4/1994 | Kao et al. | 540/446 |

FOREIGN PATENT DOCUMENTS

| | | | |
|---|---|---|---|
| 507555A1 | 7/1992 | European Pat. Off. | 514/291 |
| WO9113899 | 9/1991 | WIPO | 540/456 |

OTHER PUBLICATIONS

Commonly owned U.S. patent application Ser. No. 08/160,984 filed Dec. 1, 1993.
Commonly owned U.S. patent application Ser. No. 08/259,701, filed Jun. 14, 1994.
Commonly owned U.S. patent application Ser. No. 08/224,983 filed Apr. 8, 1994.
Commonly owned U.S. patent application Ser. No. 08/259,763 filed Jun. 14, 1994.
Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

*Primary Examiner*—Robert T. Bond
*Attorney, Agent, or Firm*—Arnold S. Milowsky

[57] ABSTRACT

A compound of the structure

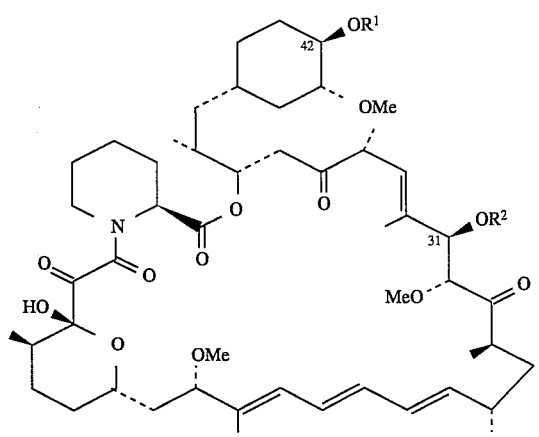

II wherein $R^1$ and $R^2$ are each, independently, hydrogen, $-CONR^3(CR^4R^5)_m(CR^4R^5)_n(CR^8R^9)_pNR^{10}R^{11}$, or $-CONR^3(CR^4R^5)_m(CR^6R^7)_n(CR^8R^9)_pNR^{10}R^{11}$, or $-CO-N\phantom{XX}N-R^{12}$, or $-CONR^3R^{13}$;

$-R^{12}$, or $-CONR^3R^{13}$;

$R^3$ is hydrogen, alkyl, or arylalkyl;

$R^4$, $R^5$, $R^8$, and $R^9$ are each, independently, hydrogen, alkyl, p—OH, —CF$_3$, or —F;

$R^6$ is hydrogen or —OR$^{13}$;

$R^7$ is hydrogen or alkyl;

$R^{10}$ is hydrogen, alkyl, or arylalkyl;

$R^{11}$, $R^{12}$, and $R^{13}$ are each independently, $-(CR^{15}R^{16})_rR^{17}$;

$R^{14}$ is hydrogen, alkyl of 1–6 carbon atoms, tri-(alkyl)silyl,

Tri-(alkyl)silyethyl, triphenylmethyl, benzyl, alkoxymethyl, tri-(alkyl)silylethoxymethyl, or tetrahydropyranyl;

$R^{15}$ and $R^{16}$ are each independently, hydrogen or alkyl;

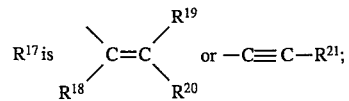

$R^{17}$ is $R^{18}$, $R^{19}$, $R^{20}$, and $R^{21}$ are each, independently, hydrogen, alkyl, halogen, or phenyl, wherein the phenyl group may be optionally mono-, di-, or tri-substituted;

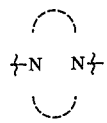

is a 5–7 membered saturated or partially unsaturated heterocyclic radical containing at least 2 ring nitrogens, wherein the heterocyclic ring may optionally contain NR$^{22}$ in the heterocyclic ring, and the ring carbons may optionally be substituted by alkyll, arylalkyl, halogen, —CF$_3$, —OR$^{14}$, or —CO$_2$R$^{10}$;

$R^{22}$ is hydrogen, alkyl, or arylalkyl;

m=0–6;

n=1–6;

p=0–6; and r=1–6
with the proviso that $R^1$ and $R^2$ are both not hydrogen, or a pharmaceutically acceptable salt thereof which is useful as an immunosuppressive, anti inflammatory, antifungal, antiproliferative, and antitumor agent.

11 Claims, No Drawings

CARBAMATES OF RAPAMYCIN

CROSS-REFERENCE TO RELATED APPLICATIONS

This application is a continuation in part of Ser. No. 08/160,984, filed Dec. 1, 1993, abandoned, which is a divisional of Ser. No. 08/054,655, filed Apr. 23, 1993 (now U.S. Pat. No. 5,302,584), which is a continuation in part of Ser. No. 07/960,597, filed Oct. 13, 1992 abandoned.

BACKGROUND OF THE INVENTION

This invention relates to carbamates of rapamycin and a method for using them for inducing immunosuppression, and in the treatment of transplantation rejection, graft vs. host disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, anti-inflammatory, antifungal, and antitumor agents.

DESCRIPTION OF THE INVENTION

This invention provides derivatives of rapamycin which are useful as immunosuppressive, antiinflammatory, antifungal, antiproliferative, and antitumor agents having the structure

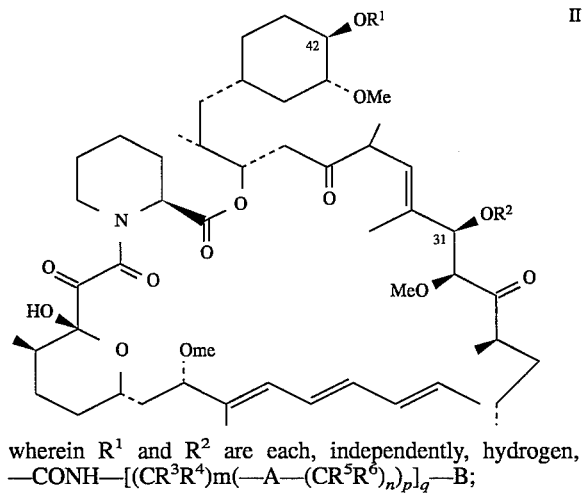

wherein $R^1$ and $R^2$ are each, independently, hydrogen, —CONH—[$(CR^3R^4)m(—A—(CR^5R^6)_n)_p]_q$—B;

$$-CO-N\begin{matrix}R^9\\R^{10}\end{matrix}, \text{ or } -CO-N\bigcirc\ ;$$

$R^3$, $R^4$, $R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms. alkylaminoalkyl of 2–12 carbon atoms, dialkylaminoalkyl of 3–12 carbon atoms, arylalkyl of 7–10 carbon atoms, cycloalkyl of 3–8 carbon atoms, -OR 7, —$SR^7$, halogen, —CN, —$NO_2$, —$CF_3$, —$COR^7$, —$CO_2R^7$, —$CONHR^7$, —$SO_2R^7$, —$OSO_3R^7$, —$NR^7R^8$, —$NHCOR^7$, —$NHSO_2R^7$, or Ar;

$R^7$ and $R^8$ are each independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, diallcylaminoalkyl of 3–12 carbon atoms, cycloalkyl of 3–8 carbon atoms, or Ar;

$R^9$ and $R^{10}$ are each, independently, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —$CF_3$, —$COR^7$, —$CO_2R^7$, —$CONHR^7$, —$SO_2R^7$, or Ar;

A is —$CH_2$—, —$NR^7$, —O—, —S—, —SO—, —$SO_2$—, —$PR^7$—, —CO—, —NHCO—, —NHSO—, or —$P(O)(R^7)$—;

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benz[b]thiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or trisubstituted with a group selected from alkyl of 1–6 carbon atoms, arylalkyl of 7– 10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

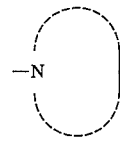

is a nitrogen containing heterocycle that may be saturated, unsaturated, or partially unsaturated, and may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$; with the proviso that $R^1$ and $R^2$ are not both hydrogen;

m=0–6;
n=0–6;
p=0–1;
q=0–1;

or a pharmaceutically acceptable salt thereof.

The pharmaceutically acceptable salts are those derived from such inorganic cations such as sodium, potassium, and the like; organic bases such as: mono-, di-, and trialkyl amines of 1–6 carbon atoms, per alkyl group and mono-, di-, and trihydroxyalkyl amines of 1–6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the aryl portion of the arylalkyl substituent is a phenyl, piperazinyl, piperidinyl, or pyridyl group that is optionally mono-, di-, or trisubstituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —$SO_3H$, —$PO_3H$, and —$CO_2H$. The term alkyl includes both straight chain and branched alkyl groups.

It is preferred that

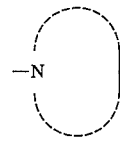

is a pyridyl, pyrazinyl, piperidinyl, morpholinyl, piperazinyl, pyrrolidinyl, thiazolyl, pyrimidinyl, isoxazolyl, pyrrolidinyl, or imidazolyl group that may be optionally substituted as described above.

This invention also discloses preferred alkenyl and alkynylamino carbamates having the structure

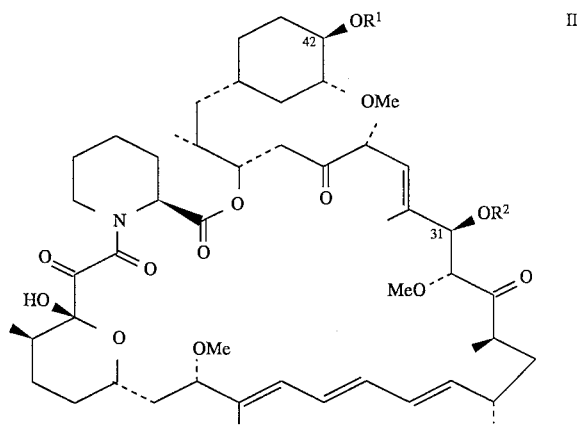

wherein $R^1$ and $R^2$ are each, independently, hydrogen,
—$CONR^3(CR^4R^5)_m(CR^6R^7)_n(CR^8R^9)_pNR^{10}R^{11}$, —$CONR^3(CR^4R^5)_m(CR^6R^7)_n(CR^8R^9)_pNR^{10}R^{11}$, or —CO—N⌒N—$R^{12}$, or —$CONR^3R^{13}$;

$R^3$ is hydrogen, alkyl of 1–6 carbon atoms, or arylalkyl of 4–10 carbon atoms;

$R^4$, $R^5$, $R^8$, and $R^9$ are each, independently, hydrogen, alkyl of 1–6 carbon atoms, —OH, —$CF_3$, or —F;

$R^6$ is hydrogen or —$OR^{14}$;

$R^7$ is hydrogen or alkyl of 1–6 carbon atoms;

$R^{10}$ is hydrogen, alkyl of 1–6 carbon atoms, or arylalkyl of 4–10 carbon atoms;

$R^{11}$, $R^{12}$, and $R^{13}$ are each, independently, —$(CR^{15}R^{16})_rR^{17}$;

$R^{14}$ is hydrogen, alkyl of 1–6 carbon atoms, tri-(alkyl of 1–6 carbon atoms)silyl, tri-(alkyl of 1–6 carbon atoms)silylethyl, triphenylmethyl, benzyl, alkoxymethyl of 2–7 carbon atoms, tri-(alkyl of 1–6 carbon atoms)silylethoxymethyl, or tetrahydropyranyl;

$R^{15}$ and $R^{16}$ are each, independently, hydrogen or alkyl of 1–6 carbon atoms;

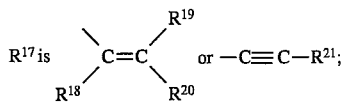

$R^{18}$, $R^{19}$, $R^{20}$, and $R^{21}$ are each, independently, hydrogen, alkyl of 1–6 carbon atoms, halogen, or phenyl, wherein the phenyl group may be optionally mono-, di-, or tri-substituted with a group selected from alkyl of 1–6 carbon atoms, arylalkyl of 7–10 carbon atoms, alkoxy of 1–6 carbon atoms, trifluoroalkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

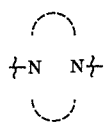

is a 5–7 membered saturated or partially unsaturated heterocyclic radical containing at least 2 ring nitrogens, wherein the heterocyclic ring may optionally contain $NR^{22}$ in the heterocyclic ting, and the ting carbons may optionally be substituted by alkyl of 1–6 carbon atoms, arylalkyl of 4–10 carbon atoms, halogen, —CF$_3$, —OR$^{14}$, or —CO$_2$R$^{10}$;

$R^{22}$ is hydrogen, alkyl of 1–6 carbon atoms, or arylalkyl of 4–10 carbon atoms;

m=0–6;

n=1–6;

p=0–6; and r=1–6 with the proviso that $R^1$ and $R^2$ are both not hydrogen, or a pharmaceutically acceptable salt thereof.

For the compounds having structure II (immediately above), the term alkyl of -6 carbon atoms, includes both straight chain as well as branched carbon chains. When any of the generic terms (i.e., CR$^4$R$^5$) are contained more than once in a given compound, each may be the same or different. The pharmaceutically acceptable salts of the compounds having structure II are the same as was defined following the compounds of structure I. It is preferred that the aryl portion of the arylalkyl substituent is a phenyl, piperazinyl, piperidinyl, or pyridyl group that is optionally mono-, di-, or tri- substituted with a group selected from alkyl of 1–6 carbon atoms, arylalkyl of 7–10 carbon atoms, alkoxy of 1–6 carbon atoms, trifluoroalkoxy of 1–6 carbon atoms, cyano, halo, nitro, carbalkoxy of 2–7 carbon atoms, tri-fluoromethyl, amino, dialkylamino of 1–6 carbon atoms per alkyl group, alkylthio of 1–6 carbon atoms, —SO$_3$H, —PO$_3$H, and —CO$_2$H.

For the compounds of structure II in which $R^1$ and/or $R^2$ is

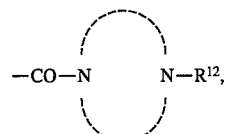

it is preferred that the

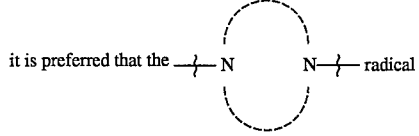

is tetrahydroimidazolyl, 1,4,5,6-tetrahydropyrimidinyl, piperazinyl, hexahydro-1,3,5-triazinyl, or homopiperazinyl, which may be optionally substituted one or more of the ring carbons by an alkyl of 1–6 carbon atoms, arylalkyl of 4–10 carbon atoms, halogen, —CF$_3$, —OR$^{13}$, or —CO$_2$R$^{10}$ substituent. It is more preferred that the above radical is piperazinyl.

Preferred compounds of this invention include those in which $R^2$ is hydrogen; those in which $R^2$ is hydrogen and the sum of m, n, and p is 1–6; and those in which $R^2$ is hydrogen, the sum of m, n, and p is 1–6, and r is 1.

The compounds of this invention carbamylated at the 42-position or at both the 31- and 42-positions can be prepared by converting the 42- and/or 31-alcohols of rapamycin to a carbonate (see Example 1) followed by reaction with an appropriately substituted amine to provide the desired carbamate. Alternatively, the compounds of this invention carbamylated at the 42-position or at both the 31- and 42-positions can be prepared by reacting rapamycin with an appropriately substituted isocyanate under neutral conditions or in the presence of a base, such as pyridine. Preparation of carbamates of rapamycin using isocyanate starting materials was disclosed in U.S. Pat. No. 5,118,678, which is hereby incorporated by reference. For the compounds of structure II, it is preferred that the carbamates are formed via the carbonate intermediate.

The 31-carbamylated compounds of this invention can be prepared by protecting the 42-alcohol of rapamycin with a protecting group, such as with a tertbutyl dimethylsilyl group, followed by carbamylation of the 31-position by the procedures described above. Removal of the protecting group provides the 31carbamylated compounds. In the case of the tert-butyl dimethylsilyl protecting group, deprotection can be accomplished under mildly acidic conditions.

Having the 31-position carbamylated and the 42-position deprotected, the 42position can be carbamylated using a different amine (via the carbonate) or isocyanate than was reacted with the 31-alcohol, to give compounds having different carbamates at the 31- and 42- positions. Alternatively, the 42-carbamylated compounds, prepared as described above, can be reacted with a different amine (via the carbonate) or isocyanate to provide compounds having different carbamates at the 31- and 42-positions.

The amines and isocyanates used to prepare the compounds of the invention are commercially available or can be prepared by methods that are disclosed in the literature.

This invention also covers analogous carbamates of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 42-oxorapamycin [U.S.

Pat. No. 5,023,2621; 29-desmethylrapamycin [U.S. Pat. No. 5,093,339, 32-desmethylrapamycin under C.A. nomenclature]; 7,29-bisdesmethylrapamycin [U.S. Pat. No. 5,093, 338, 7,32-desmethylrapamycin under C.A. nomenclature[; and 15-hydroxy- and 15,27-bishydroxy-rapamycin [U.S. Pat. No. 5,102,876]. The disclosures in the above cited U.S. Patents are hereby incorporated by reference.

This invention additionally covers derivatives of rapamycin in which one of the 31- or 42-hydroxyl groups has been converted to a carbamate, as described above, and the other of the 31- or 42-hydroxyl groups has been esterified with a moiety that it is not an allyl or propargylamino carbamate. Such other esters include acyl derivatives of rapamycin as described in U.S. Pat. No. 4,316,885, which is hereby incorporated by reference; fluorinated esters of rapamycin as described in U.S. Pat. No. 5,100,883, which is hereby incorporated by reference; amide esters of rapamycin as described in U.S. Pat. No. 5,118,677, which is hereby incorporated by reference; carbamates of rapamycin as described in U.S. Pat. No. 5,118,678, which is hereby incorporated by reference; aminoesters of rapamycin as described in U.S. Pat. No. 5,130,337, which is hereby incorporated by reference; ethers and acetals of rapamycin as described in U.S. Pat. No. 5,151,413, which is hereby incorporated by reference; aminoacyl esters of rapamycin as described in U.S. Pat. No. 4,650,803, which is hereby incorporated by reference; sulfonates and sulfamates of rapamycin as described in U.S. Pat. No. 5,117,203, which is hereby incorporated by reference; silyl ethers of rapamycin as described in U.S. Pat. No. 5,120,842, which is hereby incorporated by reference; and sulfonylcarbamates of rapamycin as described in U.S. Pat. No. 5,194,447, which is hereby incorporated by reference. Similarly, this invention covers compounds in which one hydroxyl of rapamycin has been converted to an allyl or a propargyl amino carbamate and the other hydroxyl is an inorganic ester of the hydroxyl group. These esters include phosphate, nitrate, sulfinate, sulfonate esters, and the like, and organic esters of these inorganic acids.

Immunosuppressive activity for representative compounds of this invention was evaluated in an in vitro standard pharmacological test procedure to measure lymphocyte proliferation (LAF) and two in vivo standard pharmacological test procedures. The pinch skin graft test procedure measures the immunosuppressive () activity of the compound tested as well as the ability of the compound tested to inhibit or treat transplant rejection. The adjuvant arthritis test procedure, which measures the ability of the compound tested to inhibit immune mediated inflammation, is a standard pharmacological test procedure for rheumatoid arthritis. The procedures for these standard pharmacological tests are provided below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from nondrug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 0.48 and 1.1 nM. The results obtained for the representative compounds of this invention are provided as $IC_{50}$s and are also expressed as a ratio compared with rapamycin. A positive ratio indicates immunosuppressive activity. A ratio greater than 1 indicates that the test compound inhibited thymocyte proliferation to a greater extent than rapamycin. Calculation of the ratio is shown below.

$$\frac{IC_{50} \text{ of Rapamycin}}{IC_{50} \text{ of Test Compound}}$$

Representative compounds of this invention were also evaluated in an in vivo test procedure designed to determine the survival time of pinch skin graft from male BALB/c donors transplanted to male $C_3H(H-2K)$ recipients. The method is adapted from Billingham R. E. and Medawar P. B., J. Exp. Biol. 28:385–402, (1951 ). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered ms the rejection day. The mean graft survival time (number of days±S.D.) of the drug treatment group was compared with the control group. The following Table shows the results that were obtained. Results are expressed as the mean survival time in days. Untreated (control) pinch skin grafts are usually rejected within 6–7 days. The results shown in Table 1 are based on a dose of 4 mg/kg of test compound. A survival time of 11.67+0.63 days was obtained for rapamycin at 4 mg/kg.

The following table summarizes the results obtained with representative compounds of this invention in these two standard test procedures.

TABLE 1

EVALUATION OF IMMUNOSUPPRESSIVE ACTIVITY

| Compound | LAF $IC_{50}$ nM | ratio* | Skin Graft (days ± SD)** |
|---|---|---|---|
| Example 2 | 2.1 | 0.20 | 10.2 ± 0.4 |
| Example 3 | 0.9 | 1.2 | |
| Example 4 | 0.7 | 0.9 | 10.7 ± 0.5 |
| Example 5 | 0.1 | 7.0 | 11.2 ± 0.45 |
| Example 6 | 1.4 | 0.79 | 11.0 ± 0.89# |
| Example 7 | 1.31 | 0.37 | 10.17 ± 0.98# |
| Example 8 | 0.92 | 0.83 | |
| Example 9 | 1.3 | 0.58 | |
| Example 10 | 0.7 | 1.3 | 11.20 ± 0.8 |
| No Treatment | | | 7.00 ± 0.00 |

*Vide supra for the calculation of the ratio.
** data obtained in Chremophor
data obtained in water The results of these standard pharmacological test procedures demonstrate immunosuppressive activity both in vitro and in vivo for the compounds of this invention. Positive ratios in the LAF test procedures indicates suppression of T-cell proliferation, thereby demonstrating the immunosuppressive activity of the compounds of this invention. As transplanted pinch skin grafts are typically rejected within 6–7 days without the use of an immunosuppressive agent, the increased survival time of the skin graft when treated with the compounds of this invention further demonstrates their utility as immunosuppressive agents and as agents useful for treating and preventing transplantation rejection and graft vs. host disease.

The adjuvant arthritis standard pharmacological test procedure measures the ability of test compounds to prevent immune mediated inflammation and inhibit or treat rheumatoid arthritis. The following briefly describes the test procedure used. A group of rats (male inbread Wistar Lewis rats) are pre-treated with the compound to be tested (1 h prior to antigen) and then injected with Freud's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23, and 30. The difference in paw volume (mL) from day 16 to day 0 is determined and a percent change from control is obtained. The left hind paw (uninjected paw) inflammation is caused by T-cell mediated inflammation and is recorded in Table 2 (compounds of examples 5 and 6). The right hind paw inflammation, on the other hand, is caused by nonspecific inflammation. The results are expressed as $ED_{50}$s determined from the percent change in the uninjected paw versus control at day 16 and 30; the lower the $ED_{50}$, the more potent the compound. Rapamycin $ED_{50}$ values at days 16 and 30, are provided for comparison.

TABLE 2

DEVELOPING ADJUVANT ARTHRITIS MODEL IN RATS

| Compound | Day 16 $ED_{50}$* | Day 30 $ED_{50}$* |
|---|---|---|
| Rapamycin | 0.59 | 0.55 |
| Example 5 | 0.75 | 0.60 |
| Example 6 | 1.04 | 1.15 |

*Data obtained in a 1:50 dilution of 1% Tween 80 in PHOSAL PG-50 (phospholipid concentrate with 1,2-propylene glycol, A. Nattermann & Cie. GmbH)

The results obtained in the adjuvant arthritis standard pharmacological test procedure as presented in Table 2, further demonstrated the activity of the compounds of this invention to treat or inhibit rheumatoid arthritis.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografis, and hart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Because of the activity profile obtained, the compounds of this invention also are considered to have antitumor, antifungal activities, and antiproliferative activities. The compounds of this invention therefore are also useful in treating solid tumors, adult T-cell leukemia/lymphoma, fungal infections, and hyperproliferative vascular diseases such as restenosis and atherosclerosis. When used for restenosis, it is preferred that the compounds of this invention are used to treat restenosis that occurs following an angioplasty procedure. When used for this purpose, the compounds of this invention can be administered prior to the procedure, during the procedure, subsequent t to the procedure, or any combination of the above.

The compounds of this invention provide a significant formulation advantage as they are substantially more water soluble than many other rapamycin derivatives and as such, can be advantageously formulated in water for intravenous administration. The relative oral potency in aqueous vehicle is determined by comparing the oral and i.p $ED_{50}$s obtained for representative compounds of this invention (compounds of examples 6 and 7) in the skin graft standard pharmacological test procedure. Briefly, an aqueous solution of the compound to be tested is evaluated in the skin graft test procedure so that a dose response curve can be generated for both oral and i.p. administration. An oral and i.p. $ED_{50}$ is calculated for the compound tested, and the $ED_{50}$s are expressed as a ratio according to the following formula:

$$\frac{ED_{50} \text{ oral administration}}{ED_{50} \text{ i.p. administration}}$$

When comparing oral potency for different compounds that have been evaluated, the lower the ratio, the greater the oral potency.

TABLE 3

RELATIVE POTENCY ON PROLONGATION OF MOUSE SKIN GRAFT SURVIVAL

| Compound | Water solubility mg/ml | Skin Graft po/ip ratio* |
|---|---|---|
| Example 6 | 112.3 | 8.52 |
| Example 7 | 97.5 | 5.25 |

*data obtained in water

The data in Table 3 above show that the compounds of this invention have has significantly higher water solubility than rapamycin. The increased aqueous solubility of the compounds of this invention provides advantages in the formulation and administration of the compounds of structure II.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive, antirejection, or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The compounds of this invention can be formulated neat or with a pharmaceutical carder to a mammal in need thereof. The pharmaceutical carder may be solid or liquid. When formulated orally, it has been found that 0.01% Tween 80 in PHOSAL PG-50 provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carder is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carder such as water, an organic solvent, a mixture of both or pharmaceutically acceptable oils or fats. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carder for pressurized compositions can be halogenated hydrocarbon or other pharmaceutically acceptable propellant.

Liquid pharmaceutical compositions which am sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carder may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carder, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a lungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 µg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

42-O-(4-Nitro-phenoxycarbonyl)rapamycin

To a solution of 5.15 g (5.633 mmol) of rapamycin in 40 ml of methylene chloride cooled to −78° C. with dry ice/acetone bath, was added 0.7 ml dry pyridine and 1.70 g (8.450 mmol) of p-nitrophenylchloroformate dissolved in 10 ml methylene chloride. The reaction mixture was allowed to warm to ambient and stirred overnight under nitrogen. The reaction mixture was concentrated in vacuo and partitioned between ether and water. The organic phase was washed with 0.1 N HCl (3×), then with a saturated sodium chloride solution (2×), dried over magnesium sulfate, filtered and concentrated under vacuum to give a pale yellow solid. Purification by flash column chromatography (elution with 40% then 50% ethyl acetate/hexanes) gave 5.41 g (88 %) of the title compound as a pale yellow solid. $^1$H NMR (DMSO) d 8.3 and 7.5 (aromatic-H, 4H), 4.5 (42C-H, 1H). MS(−)FAB m/z: 1078 (M$^-$), 590 (Southern Fragment).

EXAMPLE 2

Rapamycin 42-ester with methyl-(prop-2-ynyl)-carbamic acid

Under anhydrous conditions (positive nitrogen pressure, presence of molecular sieves) an ice cold mixture of 42-O-(4-nitro-phenoxycarbonyl)rapamycin (0.300 g, 0.276 mmole), N-methyl-N-propargylamine (0.048 g, 0.695 mmole), and anhydrous CH$_2$Cl$_2$ (7 ml) was allowed to slowly warm to room temperature. After overnight stirring, more amine (0.048 g, 0.695 mmole) was added. After 3 additional hours at ambient temperature, the mixture was filtered; the flitrate diluted with 150 ml of EtOAc and washed with water (3×100 ml) and brine (1×100ml), dried (K$_2$CO$_3$) and evaporated to dryness. The combined crude products from two reaction runs (from a combined 0.528 g of 42-O-(4-nitro-phenoxycarbonyl)rapamycin) were preabsorbed on silica gel and purified by flash chromatography (silica gel Merck 60, step gradient from 10 to 50% ethyl acetate in hexane. The clean fractions were evaporated and dried in vacuo to yield 0.280 g of the desired product.

$^1$H NMR (CDCl$_3$, 400MHz): δ1.625 (s, 3H, 6—CH$_3$), 1.736 and 1.751 (s, 3H, 30—CH$_3$), 2.269 (1H, C≡CH, side chain at 42), 2.972 (s, 3H, N—CH$_3$ ), 3.138 (s, 3H, 41—CH$_3$O), 3.332 (s, 3H, 7—CH$_3$O), 3.401 (s, 3H, 32—CH$_3$O), 4.575 (m, 1H, 42—CH)

$^{13}$C NMR (CDCl$_3$, 400MHz): δ215.3, 208.17, 192.52, 169.19, 166.72, 140.09, 135.99, 135.54, 133.59, 130.12, 129.51, 126.55, 126.36, 99.44, 84.76, 84.29, 81.27, 75.46, 71.86, 67.14, 59.25, 57.79, 55.85, 51.23, 46.56, 44.19, 41.69, 40.66, 40.17, 38.88, 38.30, 38.04, 36.17, 35.06, 33.72, 33.26, 32.94, 31.27, 30.26, 27.22, 27.01, 25.26, 21.46, 20.63, 16.21, 16.03, 15.91, 13.66, 13.19, 10.13 MS (neg.ion FAB, m/z): 1008.5 [M]$^-$, 590.3

EXAMPLE 3

Rapamycin 42-ester with [2-(methyl-prop-2-ynyl-amino)-ethyl]-carbamic acid

Step A.
2-[2-(Methyl-prop-2-ynyl-amino)-ethyl]-isoindole-1,3-dione

A mixture of bromoethylphthalimide (20.23 g, 0.080 mol), N-methyl-N-propargyl amine ( 5.0 g, 0.072 mol), potassium carbonate ( 17.5 g, 0.126 mol), and toluene (80 ml) was refluxed for 8 hours, filtered and the insoluble material washed with toluene. After removal of the solvent, the residue was purified by flash chromatography ( Merck 60 silica gel, step gradient from pure dichloromethane to 4% methanol in dichloromethane). The pure fractions were combined, evaporated under reduced pressure, dried in vacuo to provide 16.24 g of title product.

$^1$H NMR (400 MHz, DMSO-d$_6$): δ 2.20 (s, 3H, NCH$_3$), 2.60 (t, 2H, J 6.2 Hz CCH$_2$N—), 3.09 (t, 1H, J 2.42 Hz, C≡CH, 3.30 (d, 2H, J 2.41 Hz, NCH$_2$C≡CH), 3.65 (t, 2H, J 6.2 Hz, phthalimide NCH$_2$), 7.81–7.87 (m, 4H, H arom)

MS (EI, m/z): 242 [M]$^+$

Step B.
N1-Methyl-N1-prop-2-ynyl-ethane-1,2-diamine dihydrochloride and (E)-N1-( 3-chloro-allyl)-N1-methyl-ethane-1,2-diamine dihydrochloride A mixture of the phthalimide (16.0 g, 0.066 mol, prepared according to Step A), water (30 ml) and conc. hydrochloric acid (75 ml) was refluxed for 14 hours, cooled to ambient temperature and the insoluble material removed by filtration. The filtrate was diluted with water (100 ml), washed with ethyl acetate (150 ml) and dichloromethane (150 ml), basified with NaOH (15 ml, 50% solution), and extracted with ether (250 ml). The ether extracts were dried (MgSO$_4$) and evaporated to a smaller volume (100 ml). HCl gas was bubbled through the cold ethereal solution until pH 3 (by litmus paper ) was reached. The mixture was evaporated to dryness; further drying in vacuo provided 1.9 g (17%) of a mixture of title compound [MS (pos. ion DCI, m/z): 113 [M+H]$^+$]and N$^1$-(3-chloro-allyl)-N$^1$-methyl-ethane-1,2-diamine [MS (pos. ion DCI. m/z): 151/149 [M$^+$H]$^+$].

Step C. Rapamycin 42-ester with 12-(methyl-prop-2-ynyl-amino)-ethyl] carbamic acid Under anhydrous conditions (positive nitrogen pressure, presence of 3Å molecular sieves), a mixture of 42-O-(4-nitro-phenoxycarbonyl)rapamycin (1.0 g, 0.927 mmole), the amine hydrochloride (0.431 g, 2.31 mmole, crude mixture prepared according to Step B), DMAP (0.396 g, 3.24 mmole), and anhydrous DMF (10 ml) was stirred for two hours at room temperature. The mixture was filtered and diluted with 250 ml of ethyl acetate; the solution was washed with water (5×100 ml), brine (1× 100ml), dried (MgSO$_4$), and evaporated to dryness. The crude product was preabsorbed on silica gel and purified by flash chromatography (silica gel Merck 60, step gradient from ethyl acetate/hexane 40:60 to pure ethyl acetate to ethyl acetate/methanol 94:6). The clean fractions were combined, evaporated, and dried in vacuo to yield 0.278 g of the title product.

$^1$H NMR (CDCl$_3$, 400 MHz): δ 1.654 (s, 3H, 6—CH$_3$), 1.747 (3H, 30—CH$_3$), 2.23 (t, 1H, C≡CH, 2.30 (s, 3H, N—CH$_3$), 2.57 (t, 2H, —NCH$_2$C on the side chain at C42), 3.14 (s, 3H, 41—CH$_{3O}$), 3.332 (s, 3H, 7—CH$_{3O}$),3.337 (s, 2H, NCH$_2$C≡CH), 3.38 (s, 3H, 32—CH$_3$O), 4.55 (m, 1H, 42—CH), 5.17 (m, 1H, carbamate NH on the side chain at C42)

$^{13}$C NMR (CDCl$_3$, 400MHz): δ 215.35, 208.16, 192.47, 169.18, 166.72, 156.16, 140.12, 135.99, 135.49, 133.61, 130.09, 129.54, 126.57, 126.33, 98.44, 84.79, 84.31, 81.06, 73.25, 67.13, 59.27, 57.26, 55.90, 55.84, 54.32, 51.23, 46.56, 45.56, 44.18, 41.43, 41.20, 40.67, 40.18, 38.85, 38.35, 38.13, 35.96, 35.05, 33.71, 33.24, 32.93, 31.31, 31.23, 30.23, 27.22, 27.00, 25.26, 21.47, 20.63, 16.20, 16.04, 15.92, 15.22, 13.68, 13.13, 10.12

MS (neg. ion FAB, m/z): 105 1.3 [M]$^-$, 590.2,459.3

EXAMPLE 4

Ryamycin 42-ester with (E)-{2-[(3-chloro-allyl)-methyl-amino]-ethyl}-carbamic acid Under anhydrous conditions (positive nitrogen pressure, presence of 3Å molecular sieves), a mixture of 42-O-(4-nitro-phenoxycarbonyl)rapamycin (1.0 g, 0.927 mmole), the amine dihydrochloride (0.431 g, 2.31 mmole, crude mixture prepared according to Step B, Example 21, DMAP (0.396 g, 3.24 mmole), and anhydrous DMF (10 ml) was stirred for two hours at room temperature. The mixture is filtered and diluted with 250 ml of ethyl acetate; the solution was washed with water (5 ×100 ml), brine (1×100ml), dried (MgSO$_4$), and evaporated to dryness. The crude product was preabsorbed on silica gel and purified by flash chromatography (silica gel Merck 60, step gradient from ethyl acetate/hexane 40:60 to pure ethyl acetate to ethyl acetate/methanol 94:6). The clean tractions were combined, evaporated, and dried in vacuo to yield 0.173 g of the title product.

$^1$H NMR (CDCl$_3$, 400 MHz): δ 1.654 (s, 3H, 6—CH$_3$), 1.752 (3H, 30—CH$_3$), 2.24 (s, 3H, N—CH$_3$), 2.51 (2H, —NCH$_2$C on the side chain at C42), 3.14 (s, 3H, 41—CH$_3$), 3.33 (s, 3H, 7—CH$_3$O), 3.38 (s, 3H, 32—CH$_3$O), 4.55 (m, 1H, 42—CH), 5.15 (m, 1H, carbamate NH on the side chain at C$_{42}$), 5.86 (1H, C$_1$CH=C, on the side chain at C42), 6.17 (1H, —CH=C)

$^{13}$C NMR (CDCl$_3$, 400 MHz): δ 215.36, 208.20, 169.21, 156.19, 140.14, 136.01, 133.63, 130.12, 129.55, 126.57, 126.37, 120.67, 84.80, 84.33, 81.06, 67.16, 59.28, 55.87, 55.74, 53.63, 51.25, 46.58, 44.21, 41.72, 41.46, 40.67, 40.19, 38.88, 38.37, 35.07, 33.73, 33.25, 32.96, 31.32, 31.25, 30.26, 27.24, 27.03, 25.28, 21.49, 20.65, 16.23, 16.06, 15.94, 13.69, 10.15

MS (neg. ion FAB, m/z): 1087.3 [M]$^-$, 590.3, 495.3

EXAMPLE 5

Rapamycin 42-ester with
[3-(methyl-prop-2-ynyl-amino)-propyl-1-carbamic acid

Step A.
2-[3-(Methyl-prop-2-ynyl-amino)-propyl]-isoindole-1,3-dione

A mixture of bromopropylphthalimide (15.51 g, 0.058 mol), N-methyl-N-propargyl amine (5.0 g, 0.072 mol), potassium carbonate (12.0 g, 0.087 mol), and toluene (40 ml) was refluxed for 4 hours, filtered and the insoluble washed with toluene. After removal of the solvent, the residue was dried in vacuo to provide 14.3 g of title product.

$^1$H NMR (400 MHz, CDCl$_3$): δ 1.81 (m, 2H, C CH$_2$C), 2.14 (t, 1H, C≡CH), 2.27 (s, 3H, NCH$_3$), 2476 (t, 2H, J 7.05 Hz, CCH$_2$N), 3.32 (d, 2H, J 2.49 Hz, NCH$_2$C≡CH), 3.73 (t, 2H, J 7.26 Hz, phthalimide NCH$_2$), 7.67–7.85 (m, 4H, H arom).

MS (pos. ion FAB, m/z): 257 [M+H]+

Step B.
N1-Methyl-N1-[prop-2-ynyl-amino-1-propane-1,3-diamine

A mixture of the phthalimide (14.3 g, 0.058 mol, from step A), water (20 ml) and conc. hydrochloric acid (50 ml) was refluxed for 9 hours, cooled to ambient temperature and filtered. The filtrate was diluted with water (50 ml), basified with ice-cold 1N-NaOH (100 ml), and extracted with dichloromethane (5×50 ml). The dried (K$_2$CO$_3$) extracts were evaporated and dried in vacuo to provide 6.0 g of title product.

$^1$H NMR (400 MHz, CDCl$_3$): δ 1.627 (m, 2H,C CH$_2$C), 2.195 (m, 1H, C≡CH), 2.29 (s, 3H, NCH$_3$), 2.47 (t, 2H, J 7.2 Hz, CH$_2$N-), 2.76 (t, 2H, J 7 Hz, NCH$_2$C), 3.32 (m, 2H, NCH$_2$C≡CH).

Step C. Rapamycin 42-ester with [3-(methyl-prop-2-ynyl-amino)-propyl]-carbamic acid Under anhydrous conditions (positive nitrogen pressure, presence of 3Å molecular sieves) an ice cold mixture of 42-O-(4-nitro-phenoxycarbonyl)rapamycin (0.350 g, 0.324 mmole), amine (0.119 g, 0.945 mmole, from Step B), and anhydrous CH$_2$Cl$_2$ (8 ml) was gradually warmed to ambient temperature with stirring. After 4 hours more amine (0.119g, 0.945 mmole) was added, the mixture is stirred 2 additional hours at ambient temperature and filtered. The flitrate was diluted with 150 ml of ethyl acetate, washed with water (3×100 ml), brine (1×100ml), dried (K$_2$CO$_3$), and evaporated to dryness. The combined crude products from two experiments (for a combined 0.550 g of rapamycin 42-carbonate) were preabsorbed on silica gel and purified by flash chromatography (silica gel Merck 60, step gradient from 50% ethyl acetate in hexane to pure ethyl acetate to 3% methanol in ethyl acetate). The clean fractions were combined, evaporated, and dried in vacuo to yield 0.299 g of title product.

$^1$H NMR (CDCl$_3$, 400 MHz): δ 1.63 (s, 3H, 6—CH$_3$), 1.73 (s, 3H, 30—CH$_3$), 2.20 (t, 1H, C≡CH, side chain at 42), 2.28 (s, 3H, N—CH$_3$, side chain at 42), 3.12 (s, 3H, 41—CH$_3$O), 3.31 (s, 3H, 7—CH$_3$O), 3.36 (s, 3H, 32—CH$_3$O), 4.55 (m, 1H, 42—CH) $^{13}$C NMR (CDCl$_3$,400 MHz): δ 215.37, 208.21, 169.25, 166.79, 156.27, 140.18, 136.05, 133.66, 130.15, 129.58, 126.62, 126.40, 98.50, 84.86, 84.34, 81.14, 75.48, 73.11, 67.18, 59.27,57.37, 56.25, 55.85, 53.66, 51.27, 46.57, 45.62, 44.20, 41.62, 40.68, 40.20, 38.90, 38.40, 36.10, 35.08, 33.73, 33.28, 33.00, 31.31, 31.25, 30.27, 27.24, 27.10, 27.01, 25.27, 21.47, 20.64, 16.20, 16.04, 15.91, 13.70, 13.14, 10.13, MS (neg. ion FAB, m/z): 1065.6 [M]$^-$, 590.4, 473.4

EXAMPLE 6

Rapamycin 42-ester with
[3-(methyl-prop-2-ynyl-amino)-propyl]-carbamic acid methanesulfonate salt Under anhydrous conditions (positive nitrogen pressure, presence of 3Å molecular sieves) a solution of the free base of Example 5 (1.0g, 0.938 mmol) in 200 ml of anhydrous ether was treated with a freshly prepared ethereal solution of methanesulfonic acid (0.085 g, 0.890 mmole, conc. 4.61 mg/ml) over a 2 min. period. After 30 min., the precipitate was collected under nitrogen and dried in vacuo to provide a quantitative yield of title product.

$^1$H NMR (CDCl$_3$, 400 MHz): δ 1.65 (s, 3H, 6—CH$_3$), 1.75 (3H, 30—CH$_3$), 2.71 (t, 1 H, C≡CH, side chain at 42), 2.81 (s, 3H, N—CH$_3$, side chain at 42), 2.92 (s, 3H, CH$_3$SO$_2$), 3.14 (3H, 41—CH$_3$O), 3.33 (3H, 7—CH$_3$O), 3.38 (3H, 32—CH$_3$O), 4.55 (m, 1H, 42—CH)

$^{13}$C NMR (CDCl$_3$, 400 MHz): δ 215.26, 208.17, 169.24, 166.74, 156.79, 140.59, 140.07, 136.18, 136.07, 133.57, 130.16, 129.49, 126.54, 126.42, 98.49, 84.36, 81.08, 80.20, 75.53, 70.43, 67.19, 59.25,57.37, 55.86, 52.33, 51.26, 46.56, 44.19, 41.46, 40.30, 40.21, 39.13, 38.99, 38.31, 37.44, 35.82, 35.07, 33.79, 33.19, 32.88, 31.22, 30.15, 27.23, 27.04, 25.27, 24.78, 21.48, 20.65, 16.20, 16.02, 15.88, 13.68, 13.22, 10.16

MS (neg. ion FAB, m/z): 1065.5 [M]–, 590.3, 473.3

EXAMPLE 7

Rapamycin 42-ester with
[3-(methyl-prop-2-ynyl-amino)-propyl]-carbamic acid hydrochloride salt Under anhydrous conditions (positive nitrogen pressure, presence of molecular sieves), a solution of the free base of Example 5 (1.10 g, 1.03 mmol) in 50 ml of anhydrous ether was treated dropwise with a 1N ethereal hydrochloric acid (0.98 ml, 0.98 mmole) over a 15 min. period. The mixture was sonicated for an additional 20 min., the precipitate was collected under nitrogen and dried in vacuo to get a quantitative yield of title product.

$^1$H NMR (CDCl$_3$, 400 MHz): δ 1.65 (s, 3H, 6—CH$_3$), 1.75 (3H, 30—CH$_3$), 2.71 (t, 1H, C≡CH, side chain at 42), 2.85 (s, 3H, N—CH$_3$, side chain at 42), 3.14 (3H, 41—CH$_3$O), 3.33 (3H, 7—CH$_3$O), 3.38 (3H, 32—CH$_3$O), 4.55 (m, 1H, 42—CH) $^{13}$C NMR (CDCl$_3$, 400 MHz): d 215.37, 208.22, 192.65, 169.25, 166.77, 156.66 , 140.12, 136.09, 133.62, 130.16, 129.52, 126.58, 126.40, 98.48, 84.82, 84.31, 81.11,80.21, 75.56, 70.36, 67.16, 59.26, 55.84, 51.87, 51.23, 46.55, 44.17, 41.42, 40.65, 40.19, 39.91, 38.87, 38.26, 37.46, 35.75, 35.05, 33.74, 33.16, 32.89, 32.84, 31.37, 31.20, 30.14, 27.20, 27.02, 25.25, 24.76, 21.46, 20.62, 16.18, 16.00, 15.86, 13.66, 13.16, 10.12

MS (neg. ion FAB, m/z): 1065.8 [M]⁻, 590.5, 473.5

EXAMPLE 8

Rapamycin 42-ester with [2-hydroxy-3-(methyl-prop-2-ynyl-amino)-propyl]-carbamic acid Step A.
2-[2-Hydroxy-3-(methyl-prop-2-ynyl-amino)-propyl]-isoindole-1,3-dione A mixture of epichlorohydrin (6.03 g, 5.1 ml, 0.065 mole), 0.1 ml of pyridine and N-methyl-N-propargylamine (4.095 g, 0.059 ml, 0.059 mole) in 15 ml of anhydrous methanol was stirred for 2 hours at 40°–45° C. After stirring overnight at ambient temperature, the TLC (hexane-THF 6:4, UV) showed that the starting amine was practically consumed. The solvent was evaporated and the crude product dissolved in 50 ml of anhydrous DMF. Potassium phthalimide (12.57 g, 0.068 mole) was added and the mixture refluxed for 8 hours. TLC (dichloromethane/methanol 95:5, UV, $I_2$) showed formation of a new product with Rf 0.26. The mixture was filtered cold and the filtrate diluted with 30{) ml of EtOAc. The solution was washed with water (10×200 ml), brine (1×200m ml) and dried (MgSO₄). After removal of the solvent, the residue was preabsorbed on Merck silica gel-60 and purified by flash chromatography (step gradient from 0 to 5% methanol in dichloromethane). The pure fractions were combined, evaporated and dried in vacuo to yield an off white solid (6.6 g).

¹NMR (DMSO-d₆, 400 MHz): δ 2.22 (s, 3H, NCH₃), 2.39 (m, 2H, NCH₂), 3.09 (t, 1H, C≡CH), 3.58 (m, 2H, CH₂), 3.88 (m, 1H, CHO), 4.92 (d, 1H, OH), 7.83 (m, 4H, H arom)

MS (DCD m/z: 273 [M+H]⁺; (EI) m/z: 272 [M]⁺

Step B.
1-Amino-3-(methyl-prop-2-ynyl-amino)-propan-2-ol dihydrochloride

The phthalimide (6.6 g, 0.024 mole, prepared according to Step A) dissolved in 50 ml of anhydrous ethanol was treated with hydrazine hydrate (1.21 g, 1.18 ml, 0.024 mole) in one portion. The mixture was refluxed for 1 hour, cooled to 0° C., and filtered. The filtrate was evaporated on rotary evaporator to a volume of approximately 15 ml, acidified with 4N HCl in dioxane (0.06 ml, 0.025 mole), and sonicated. The precipitate was filtered at 0° C. and dried in vacuo to provide the title product as an off-white solid 5.1 g. It was used as such in the next step. MS (DCI, m/z: 143 [M+H]⁺

Step C. Rapamycin 42-ester with [2-hydroxy-3.(methylrprop-2-ynyl-amino)-propyl]-carbamic acid A mixture of 42-O-(4-nitro-phenoxycarbonyl)rapamycin (0.750 g, 0.695 mmole), the amine dihydrochloride (0.448 g, 2.065 mmole, from step B), DMAP (0.339 g, 2.78 mmole) and anhydrous DMF (10 ml) was stirred at ambient temperature for 2.5 hours. The reaction mixture was filtered and the flitrate diluted with 250 ml of EtOAc. The solution was washed with water (5×100 ml), brine (1×100 ml), dried (MgSO₄) and evaporated to dryness. The crude product was preabsorbed on Mercksilica gel-60 and purified by flash chromatography (step gradient from EtOAc-hexane 80:20 to pure EtOAc, to EtOAc-MeOH 97:3). The clean fractions were combined, evaporated and dried in vacuo to yield 0.410 g (54.5 %) of desired product, m.p. 97°–105° C. (softens at 92° C.).

¹H NMR (CDCl₃, 400 MHz): δ 1.653 (s, 3H, 6—CH₃), 1.733 and 1.749 (3H, 30—CH₃), 2.245 (t, 1H, C≡CH, side chain at 42), 2.356 (s, 3H, NCH₃, side chain at 42, 3.139 (s, 3H, 41—CH₃O), 3.32 (s, 3H, 7—CH₃O), 3.384 (s, 3H, 32—CH₃O), 3.765 (m, 1H, CHO, side chain at 42), 4.56 (m, 1H, 42—CH)

¹³C NMR (CDCl₃, 400 MHz): δ 215.30, 208.13, 192.48, 169.16, 166.70, 156.54, 140.08, 135.97, 135.50, 133.58, 130.94, 129.50, 126.55, 126.34, 98.43, 86.39, 84.76, 84.28, 81.08, 73.44, 67.11, 59.24, 58.44, 58.36, 55.82, 51.21, 46.54, 46.05, 46.03, 44.16, 41.63, 41.42, 40.65, 40.16, 38.85, 38.31, 35.95, 35.55, 35.13, 33.70, 33.22, 32.89, 31.21, 31.17, 27.20, 26.99, 25.24, 21.45, 20.61, 1.6.18, 16.01.15.88, 13.65, 13.12, 10.10

MS (neg. ion FAB m/z): 108 1.7 [M]⁻, 590.3, 489.3

EXAMPLE 9

Rapamycin 42-ester with 4-(prop-2-ynyl)-piperazine-1-carboxylic acid

Under anhydrous conditions (positive nitrogen pressure, presence of 3Å molecular sieves) a mixture of 42-O-(4-nitro-phenoxycarbonyl)rapamycin (0.500 g, 0.463 mmole), amine dihydrochloride (0.183 g, 0.927 mmole), DMAP (0.169 g, 1.389 mmole), and anhydrous DMF (10 ml) was stirred for 3.5 hours and filtered. The filtrate was diluted with 200 ml of ethyl acetate and washed with water (4×100 ml) and brine (1×100ml), dried (MgSO₄), and evaporated to dryness. The combined crude products from two batches (for a total of 0.788 g of 42-O-(4-nitrophenoxycarbonyl)rapamycin) were preabsorbed on silica gel and purified by flash chromatography (silica gel Merck 60, step gradient from 70 to 90% ethyl acetate in hexane). The clean fractions were combined, evaporated, dried in vacuo to yield 0.541 g of desired product.

¹H NMR (CDCl₃, 400 MHz): δ 1.65 (s, 3H, 6—CH₃), 1.735 and 1.752 (3H, 30—CH₃). 2.26 (t, 1H, C≡CH), 2.52 (m, 4H, CH₂N), 3.13 (s, 3H, 41—CH₃O), 3.33 (s, 3H, 7—CH₃O), 3.39 (s, 3H, 32—CH₃O), 3.53 (m, 4H, CH₂NCO), 4.57 (m, 1H, 42—CH)

¹³C NMR (CDCl₃, 400 MHz): δ 215.28, 208.13, 192.49, 169.17, 166.70, 154.93, 140.08, 135.97, 135.54, 133.57, 130.10, 129.48, 126.54, 126.34, 98.43, 86.40, 84.73, 84.27, 81.34, 78.25, 73.45, 67.12, 59.24, 57.76, 55.82, 51.48, 51.22, 46.93, 46.54, 46.02, 43.55, 41.43, 40.62, 40.15, 38.88, 38.32, 36.21, 35.06, 33.70, 33.23, 32.96, 31.25, 31.21, 30.28, 27.20, 26.99, 25.24, 21.45, 20.61, 16.18, 15.99, 15.90, 13.64, 13.13, 10.11

MS (neg. ion FAB, m/z): 1063.7 [M]⁻, 590.5, 471.4

EXAMPLE 10

Rapamycin 42-ester with [4-(methyl-prop-2-ynyl-amino)-butyl]-carbamic acid

Step A.
2-[4-(Methyl-prop-2-ynyl-amino)-butyl]-isoindole-1,3-dione

A mixture of bromobutylphthalimide (31.98 g, 0.113 mol), N-methyl-N-propargyl amine (8.19 g, 10 ml, 0.119 mol), potassium carbonate (23.39 g, 0.170 mol), and toluene (140 ml) was refluxed for 8 hours followed by overnight stirring at ambient temperature. The insoluble material was filtered off and washed with toluene. The flitrate and washings are evaporated to dryness, and the residue is purified by flash chromatography (Merck 60 silica gel, step gradient from 0–5% methanol in $CH_2Cl_2$). The pure fractions were combined, evaporated and dried in vacuo to yield the title compound, which was used as such in the next step.

$^1$NMR NMR (DMSO-$d_6$): δ 1.38 (m, 2H, $CCH_2C$), 1.57 (m, 2H, $CCH_2C$), 2.13 (s, 3H, $NCH_3$), 2.31 (t, 2H, J 7 Hz, $NCH_2C$), 3.05 (t, 1H, J 2.4 Hz, C≡CH), 3.23 (d, 2H, J 2.49 Hz, $NCH_2$C≡CH), 3.56 (t, 2H, J 7.1 Hz, phthalimido $NCH_2C$), 7.83 (m, 4H, H arom).

MS (El, m/z): 270 [M]$^+$, 160, 82

Step B.
N1-Methyl-N1-(prop-2-ynyl)-butane-1,4-diamine dihydrochloride

A mixture of the crude phthalimide (prepared as described in Step A), water (100 ml) and conc. hydrochloric acid (140 ml) was refluxed for 12 hours, cooled to ambient temperature, and filtered. Water (100 ml) was added, and the aqueous solution was washed with ethyl acetate (1×150 ml), dichloromethane (1×150 ml), and evaporated to dryness to provide 13.04 g of the title product.

$^1$H NMR (DMSO-$d_6$): δ 1.61 (m, 2H, $CCH_2C$), 1.76 (m, 2H, $CCH_2C$), 2.73 (s. 3H, $NCH_3$), 2.76 (m, 2H, $-NCH_2C$), 3.08 (m, 2H, $NCH_2C$), 3.84 (t, 1H, J 2.4 Hz, C≡CH ), 4.06 (d, 2H, J 2.19 Hz, $NCH_2$C≡CH).

Step C. Rapamycin 42-ester with [4-(methyl-prop-2-ynyl-amino)-butyl]-carbamic acid Under anhydrous conditions (positive nitrogen pressure, presence of 3Å molecular sieves) a mixture of 42-O-(4-nitro-phenoxycarbonyl)rapamycin (1.0 g, 0.927 mmole), the amine dihydrochloride of Step B (0.397 g, 1.854 mmole), DMAP (0.226 g, 1.854 mmole), and anhydrous DMF (15 ml) was stirred for two hours at room temp. The mixture was filtered and diluted with 250 ml of ethyl acetate. The solution was washed with water (5×100 ml), brine (1×100ml), dried (MgSO$_4$), and evaporated to dryness. The crude product was preabsorbed on silica gel and purified by flash chromatography (silica gel Merck 60, step gradient from ethyl acetate/hexane 25:75 to pure ethyl acetate to ethyl acetate/methanol 98:2). The clean fractions were combined, evaporated, and dried in vacuo to yield 0.423 g of title product.

$^1$H NMR (DMSO-$d_6$, 400 MHz): δ 1.654 (s, 3H, 6—$CH_3$), 1.749 and 1.736 (3H, 30—CH$_3$), 2.218 (t, 1H, C≡CH), 2.29 (s, 3H, N—$CH_3$), 2.42 (t, 2H, —$NCH_2$C on the side chain at C-42), 3.14 (s, 3H, 41—$CH_3O$), 3.33 (s, 3H, 7—$CH_3O$), 3.379 (s, 3H, 32—$CH_3O$), 4.56 (m, 1H, 42—CH), 4.99 (m, 1H, carbamate NH on the side chain at C42).

$^{13}$C NMR (DMSO-$d_6$, 400MHz): δ 215.38, 208.22, 192.55, 169.23, 166.77, 140.13, 136.03, 133.63, 130.14. 129.56, 126.60, 126.39. 98.47, 84.78, 84.32, 81.09, 73.09, 67.14, 59.26, 55.85, 55.04, 51.23, 46.56, 45.41, 41.56, 41.44, 40.66, 40.17, 38.34, 35.05, 33.70, 33.25, 32.93, 31.29, 31.23, 30.24, 27.66, 27.22, 27.00, 25.25, 24.74, 21.45, 20.62, 16.20, 16.02, 15.90, 13.65, 13.12, 10.11

MS (neg. ion FAB, m/z): 1079.3 [M]$^-$, 590.2, 487.2.

What is claimed is:
1. A compound of the structure wherein $R^1$ and $R^2$ are each, independently, hydrogen, $-CONR^3(CR^4R^5)_m(CR^6R^7)_n(CR^8R^9)_pNR^{10}R^{11}$;

$R^3$ is hydrogen, alkyl of 1–6 carbon atoms, or arylalkyl of 4–10 carbon atoms;

$R^4$, $R^5$, $R^8$, and $R^9$ are each, independently, hydrogen, alkyl of 1–6 carbon atoms, —OH, —$CF_3$, or —F;

$R^6$ is hydrogen or —$OR^{14}$;

$R^7$ is hydrogen or alkyl of 1–6 carbon atoms;

$R^{10}$ is hydrogen, alkyl of 1–6 carbon atoms, or arylalkyl of 4–10 carbon atoms;

$R^{11}$ is —$(CR^{15}R^{16})_rR^{17}$;

$R^{14}$ is hydrogen, alkyl of 1–6 carbon atoms, tri-(alkyl of 1–6 carbon atoms)silyl, tri-(alkyl of 1–6 carbon atoms)silylethyl, triphenylmethyl, benzyl, alkoxymethyl of 2–7 carbon atoms, tri-(alkyl of 1–6 carbon atoms)silylethoxymethyl, or tetrahydropyranyl;

$R^{15}$ and $R^{16}$ are each, independently, hydrogen or alkyl of 1–6 carbon atoms;

$R^{17}$ is $$\begin{matrix} R^{17}is & \diagdown \\ & C=C \\ & \diagup \quad \diagdown \\ & R^{18} \quad R^{20} \end{matrix} \begin{matrix} R^{19} \\ \diagup \\ \diagdown \end{matrix} \quad \text{or} \quad -C\equiv C-R^{21};$$

$R^{18}$, $R^{19}$, $R^{20}$, and $R^{21}$ are each, independently, hydrogen, alkyl of 1–6 carbon atoms, halogen, or phenyl, wherein the phenyl group may be optionally mono-, di-, or tri-substituted with a group selected from alkyl of 1–6 carbon atoms arylalkyl of 7–10 carbon atoms, alkoxy of 1–6 carbon atoms, trifluoroalkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

$R^{22}$ is hydrogen, alkyl of 1–6 carbon atoms, or arylalkyl of 4–10 carbon atoms;

m=0–6;

n=1–6;

p=0–6; and r=1–6 with the proviso that $R^1$ and $R^2$ are both not hydrogen, or a pharmaceutically acceptable salt thereof.

2. The compound of claim 1 wherein $R^2$ is hydrogen or a pharmaceutically acceptable salt thereof, 3. The compound of claim 2 wherein the sum of m, n, and p is 1–6 or a pharmaceutically acceptable salt thereof.

4. The compound of claim 3 wherein r=1 or a pharmaceutically acceptable salt thereof.

5. The compound of claim 1 which is rapamycin 42-ester with [2-(methyl-prop-2-ynyl-amino)-ethyl]-carbamic acid or a pharmaceutically acceptable salt thereof.

6. The compound of claim 1 which is rapamycin 42-ester with (E)-{2-[(3-chloroallyl)-methyl-amino]-ethyl}-carbamic acid or a pharmaceutically acceptable salt thereof.

7. The compound of claim 1 which is rapamycin 42-ester with [3-(methyl-prop-2-ynyl-amino)-propyl]-carbamic acid or a pharmaceutically acceptable salt thereof.

8. The compound of claim 1 which is rapamycin 42-ester with [3-(methyl-prop-2-ynyl-amino)-propyl]-carbamic acid methanesulfonate salt.

9. The compound of claim 1 which is rapamycin 42-ester with [3-(methyl-prop-2-ynyl-amino)-propyl]-carbamic acid hydrochloride salt.

10. The compound of claim 1 which is rapamycin 42-ester with [2-hydroxy-3-(methyl-prop-2-ynyl-amino)-propyl]-carbamic acid or a pharmaceutically acceptable salt thereof.

11. The compound of claim 1 which is rapamycin 42-ester with [4-(methyl-prop-2-ynyl-amino)-butyl]-carbamic acid or a pharmaceutically acceptable salt thereof.

* * * * *